United States Patent

Blasband et al.

(10) Patent No.: US 6,451,525 B1
(45) Date of Patent: Sep. 17, 2002

(54) PARALLEL SEQUENCING METHOD

(75) Inventors: Andrew J. Blasband, Redwood City, CA (US); Sandy M. Koepf, San Francisco, CA (US); Adam L. Lowe, San Francisco, CA (US)

(73) Assignee: PE Corporation (NY), Foster City, CA (US)

( * ) Notice: Subject to any disclaimer, the term of this patent is extended or adjusted under 35 U.S.C. 154(b) by 0 days.

(21) Appl. No.: 09/204,858

(22) Filed: Dec. 3, 1998

(51) Int. Cl.$^7$ .......................... C12O 1/68; C07H 21/04; C07H 21/02
(52) U.S. Cl. .................. 435/6; 435/91.1; 435/91.2; 536/24.33; 536/24.32; 536/23.1
(58) Field of Search .................. 536/24.32, 24.33, 536/23.1, 24.3; 435/6, 91.1, 91.2

(56) References Cited

U.S. PATENT DOCUMENTS

| | | | | |
|---|---|---|---|---|
| 4,942,124 A | * | 6/1990 | Church | 435/6 |
| 5,002,867 A | * | 3/1991 | Macevicz | 435/6 |
| 5,415,839 A | | 5/1995 | Zaun et al. | 422/64 |
| 5,518,900 A | * | 5/1996 | Nikiforov et al. | 435/91.1 |
| 5,935,793 A | * | 8/1999 | Wong | 435/6 |
| 5,981,176 A | | 11/1999 | Wallace | 435/6 |

FOREIGN PATENT DOCUMENTS

| WO | WO 92/15712 | 9/1992 |
|---|---|---|
| WO | WO 93/17126 | 9/1993 |
| WO | WO93/25563 | 12/1993 |
| WO | WO 94/21820 | 9/1994 |
| WO | WO 96/41011 | 12/1996 |

OTHER PUBLICATIONS

Guo et al. Direct Fluorescence analysis of genetic polymorphisms by hybridization with oligonucleotide arrays on glas support. Nucleic acid research. vol. 22, No. 24, pp. 5456–5465, Oct. 1994.*

Schena, M. et al., Parallel human genome analysis: Microarray-based expression monitoring of 1000 genes, Proc. Natl. Acad. Sci., vol. 93, 10614–10619, Oct. 1996.*

Pastinen, Tomi, et al, "Multiplex, fluorescent, solid–phase minisequencing for efficient screening of DNA sequence variation," Clinical Chemistry 42(9): 1391–1397 (1996).

Schena, Mark, et al., "Parallel human genome analysis: Microarray–based expression monitoring of 1000 genes," Proc. Natl. Acad. Sci USA 93: 10614–10619 (1996).

Shumaker, John M., et al., "Mutation Detection by Solid Phase Primer Extension," Human Mutation 7: 346–354 (1996).

Southern, Ed M., "DNA chips: analysing sequence by hybridization to oligonucleotides on a large scale," TIG Mar. 12(3): 110–115 (1996).

Syvänen, Ann–Christine, et al., "Identification of Individuals of Analysis of Biallelic DNA Markers, Using PCR and Solid–Phase Minisequencing," Am J. Genet. 52:46–59 (1993).

Syvänan, Ann–Christine, et al., "A Primer–Guided Nucleotide Incorporation Assay in the Genotyping of Apolipoprotein E," Genomics 8: 684–692 (1990).

* cited by examiner

*Primary Examiner*—Kenneth R. Horlick
*Assistant Examiner*—Cynthia B. Wilder
(74) *Attorney, Agent, or Firm*—Vincent M Powers

(57) ABSTRACT

A method for obtaining sequence information from a plurality of target polynucleotides in a sample is disclosed. In one embodiment, the method involves contacting a plurality of different sequence primers with a polynucleotide sample under conditions effective for the primers to anneal to primer-complementary regions in one or more target polynucleotides, to form one or more target-primer hybrid (s). Each different-sequence primer contains (i) a target binding segment and (ii) a tag segment having a nucleotide sequence that uniquely identifies the target binding segment. The hybrid(s) are contacted with a labeled nucleotide terminator in the presence of a primer-extending reagent, under conditions effective to append the base to an end of the annealed primer in the hybrid only when the base is complementary to a base in the target polynucleotide that is immediately adjacent to the end of the annealed primer, to form an extended hybrid mixture. The primers are then immobilized on an addressable array of immobilized, different tag complements, wherein each different tag complement contains a sequence that is complementary to the primer tag segments, under conditions effective to hybridize the primers to corresponding tag complements. The identification of a nucleotide base appended to at least one extended primer immobilized on the array allows determination of the presence of at least one target sequence in the sample.

12 Claims, No Drawings

SEQUENCE LISTING

<160> NUMBER OF SEQ ID NOS: 4

<210> SEQ ID NO 1
<211> LENGTH: 42
<212> TYPE: DNA
<213> ORGANISM: Artificial Sequence
<220> FEATURE:
<223> OTHER INFORMATION: synthetic primer Z996SP6(A)

<400> SEQUENCE: 1
tgatgattga ttgtatgatt ttgaatttag gtgacactat ag          42

<210> SEQ ID NO 2
<211> LENGTH: 47
<212> TYPE: DNA
<213> ORGANISM: Artificial Sequence
<220> FEATURE:
<223> OTHER INFORMATION: synthetic primer Z1045T7(T)

<400> SEQUENCE: 2
tgatgattaa agaaagttga gtataatacg actcactata gggcgaa     47

<210> SEQ ID NO 3
<211> LENGTH: 42

```
-continued

<212> TYPE: DNA
<213> ORGANISM: Artificial Sequence
<220> FEATURE:
<223> OTHER INFORMATION: synthetic primer Z1082m13(G)

<400> SEQUENCE: 3
tgatgatttg tagtatgtat aaagtgtaaa acgacggcca gt                    42

<210> SEQ ID NO 4
<211> LENGTH: 43
<212> TYPE: DNA
<213> ORGANISM: Artificial Sequence
<220> FEATURE:
<223> OTHER INFORMATION: synthetic primer Z1128MS(C)

<400> SEQUENCE: 4
tgatgatttt gatgtaaaag ttgaagctcg gtacccgggg atc                   43
```

PARALLEL SEQUENCING METHOD

FIELD OF THE INVENTION

The present invention relates to a method for rapidly determining sequence information for a plurality of target polynucleotides in a sample, and to reagents and kits therefor. In a particular embodiment, the invention is directed to a method of determining, in parallel, the presence or absence of a plurality of sequence variants in a sample.

References

Albretsen et al., *Anal. Biochem.* 189:40 (1990).
Ausubel et al., eds., *Current Protocols in Molecular Biology* Vol. 1, Chapter 2, Section I, John Wiley & Sons, New York (1993).
Barany et al., PCT Application No. PCT/US91/06103.
Barrett, R. W., et al., U.S. Pat. No. 5,482,867 (1996).
Beaucage and Iyer, *Tetrahedron* 48:2223–2311 (1992).
Bergot et al., PCT Application No. PCT/US90/05565 (WO 91/07507).
Boom et al., U.S. Pat. No. 5,234,809.
Brenner, PCT Publications No. WO 96/12014 and WO 96/41011.
Breslauer et al., *Proc. Natl. Acad. Sci.* 83:3746–3750 (1986).
Cantor et al, U.S. Pat. No. 5,482,836.
Chidgeavadze et al., *Nucleic Acids Res.* 12:1671–1686 (1984).
Chidgeavadze et al., *FEB. Lett.* 183: 275–278 (1985).
Chidgeavadze et al., *Biochim. Biophys. Acta* 868:145 (1986).
Dieffenbach et al., in PCR Primer: A Laboratory Manual, Dieffenbach and Dveksler, eds., pp. 133–142, CSHL Press, New York (1995).
Drmanac, R., et al., *Electrophoresis* 13:566 (1992).
Drmanac, R., et al., *Science* 260:1649 (1993).
Eckstein, F., *Oligonucleotides and Analogs: A Practical Approach*, Chapters 8 and 9, IRL Press, Oxford, GB (1991).
Fodor, S. P. A., et al., *Science* 251:767 (1991).
Fodor, S. P. A., et al., U.S. Pat. No. 5,445,934 (1995).
Fung et al, U.S. Pat. No. 4,757,141.
Gait, M. J., ed., *Oligonucleotide Synthesis: A Practical Approach*, IRL Press, Oxford, (1984; 1990)
Haugland, *Handbook of Fluorescent Probes and Research Chemicals*, Molecular Probes, Inc., Eugene, OR (1992).
Hobbs, Jr., et al., U.S. Pat. No. 5,151,507.
Ji et al., *Anal. Chem.* 65:1323–1328 (1993).
Johnston, R. F., et al., *Electrophoresis* 11:355 (1990).
Keller and Manak, *DNA Probes*, 2nd Ed., Stockton Press, New York.(1993).
Khrapko, K. R., et al., *DNA Sequencing* 1:375 (1991).
Knudsen; H., et al., *Nucleic Acids Res.* 24:494–500 (1996).
Kornberg and Baker, *DNA Replication*, 2nd Ed., W. H. Freeman, San Francisco, Calif. (1992).
Krayevski, A., et al., *Biochim. Biophys. Acta* 783:216 (1984).
Mathies, R. A., et al., U.S. Pat. No. 5,091,652 (1992).
Matthews et al, *Anal. Biochem.* 169:1–25 (1988).
Menchen et al., PCT Publication No. WO 94/05688 (1994).
Menchen et al., U.S. Pat. No. 5,188,934.
Metzker et al., *Nucleic Acids Res.* 22:4259 (1994)
Mikhailopulo et al., *FEB Lett.* 250:139 (1989)
Miller et al., *Nucleic Acids Res.* 16(3):9–10 (1988).
Montpetit et al., *J. Virol. Methods* 36:119–128 (1992).
Mullis, U.S. Pat. Nos. 4,683,195; and 4,683,202.
Osborne, *CABIOS* 8:83 (1991).
Pirrung et al., U.S. Pat. No. 5,143,854.
Ploem, J. S., in *Fluorescent and Luminescent Probes for Biological Activity*, Mason, T. W., Ed., Academic Press, London, pp. 1–11 (1993).
Pon et al., *Biotechniques* 6:768–775 (1988).
Rosenblum et al., *Nucl. Acids Res.* 25:4500–4504 (1997).
Rychlik et al., *Nucleic Acids Res.* 17:8543–8551 (1989) and 18:6409–6412 (1990).
Sambrook et al., *Molecular Cloning A Laboratory Manual.* 2nd Edition, Cold Spring Harbor Laboratory, New York (1989).
Scheit, *Nucleotide Analogs*, John Wiley Pub., New York (1980).
Schena, M., et al., *Science* 270:467 (1995).
Shalon, D., Ph.D. Dissertation, Falconer Library, Stanford University, California (1995).
Shoemaker et al., European Pub. No. EP 799,897 A1 (1997).
Uhlman and Peyman, *Chem. Rev.* 90:543–584 (1990).
Walsh et al., *Biotechniques* 10(4): 506–513 (1991).
Wetmur, *Crit. Rev. Biochem. Mol. Biol.* 26:227–259 (1991).
Yershov, G., et al., *Proc. Natl. Acad. Sci.* 93:4913 (1996).

BACKGROUND OF THE INVENTION

Genetic mutations underlie many disease states and disorders. Some diseases have been traced directly to single point mutations in genomic sequences (e.g., the A to T mutation associated with sickle cell anemia), while others have been correlated with large numbers of different possible polymorphisms located in the same or different genetic loci (e.g., cystic fibrosis). Mutations within the same genetic locus can produce different diseases (e.g., hemoglobinopathies). In other cases, the presence of a mutation may indicate susceptibility to particular condition for a disease but is insufficient to reliably predict the occurrence of the disease with certainty.

Genetic mutations have been found to occur by a variety of mechanisms, such as single base substitutions, deletions of one or more bases, insertions of one or more bases, transpositions, duplications, etc. Single base substitutions (transitions and transversions) within gene sequences can cause missense mutations and nonsense mutations. In missense mutations, an amino acid residue is replaced by a different amino acid residue, whereas in nonsense mutations, stop codons are created that lead to truncated polypeptide products. Mutations that occur within signal sequences for exon/intron splicing of mRNAs can produce defective splice variants with dramatically altered protein sequences. Deletions, insertions, and other mutations can also cause fraameshifts in which contiguous residues encoded downstream of the mutation are replaced with entirely different amino acid residues. Mutations outside of exons can interfere with gene expression and other processes. Most known pathogenic mutations have been localize to gene-coding sequences, splice signals, and regulatory sequences.

The large numbers of potential genetic polymorphisms poses a significant challenge to the development of methods for identifying and characterzing samples and for diagnosing and predicting disease. In light of the increasing quantity of sequence data that has become available for various organisms, and particularly for higher organisms such as humans, there is a need for rapid and convenient methods for simultaneously determining the presence or absence of a plurality of target mutations. Ideally, such a method should have high sensitivity, accuracy, and reproducibility. The method should allow simultaneous detection of large numbers of target mutations.

Accordingly, it is an object of the present invention to provide a precise and reproducible method for detecting a plurality of target polynucleotide sequences in a sample.

It is another object to provide a rapid and convenient method for determining the presence or absence of a plurality of target polynucleotide sequences in parallel.

It is an additional object to provide a method for establishing a sequence profile of one or more samples, which is useful for identifying or distinguishing samples.

It is yet another object to provide a method for determining the zygosity of one or more genetic loci in the sample.

Still another object is to provide a method that is useful in forensics, for establishing a sequence profile for the sample that can be used to help include or exclude a potential suspect from consideration.

It is also an object of the present invention to provide kits and reagents that are useful for practicing the above methods.

SUMMARY OF THE INVENTION

In one aspect, the present invention includes a method for obtaining sequence information from a plurality of target polynucleotides in a sample. In one embodiment, the method involves contacting a plurality of different-sequence primers with a polynucleotide sample under conditions effective for the primers to anneal to primer-complementary regions in one or more target polynucleotides, to form one or more target-primer hybrid(s). Each different-sequence primer contains (i) a target binding segment and (ii) a tag segment having a nucleotide sequence that identifies the target binding segment. The hybrid(s) are contacted with a labeled nucleotide terminator in the presence of a primer-extending reagent under conditions effective to append (covalently link) the base to an end of the annealed primer in the hybrid only when the base is complementary to a base in the target polynucleotide that is immediately adjacent to the end of the annealed primer, to form an extended hybrid mixture. Preferably, the primers are then immobilized on an addressable array of immobilized, different tag complements, wherein each different tag complement contains a sequence that is complementary t the primer tag segments, under conditions effective to hybridize the primers to corresponding tag complements. The identification of a nucleotide base appended to at least one extended primer immobilized on the array allows determination of the presence of at least one target sequence in the sample.

In one embodiment, the primer extension step includes contacting the hybrid(s) with at least two different nucleotide terminators each of which contains a detectably different label. For example, two or more nucleotide terminators may be contacted simultaneously, in the same reaction mixture, with the hybrid(s), to provide an indication of which of two or more base alternatives are present in a particular target sequence.

In another embodiment, the primer annealing and extension steps are performed on at least two sample aliquots, such that the first aliquot is annealed to a first set of different-sequence primers, to produce a first set of target-primer hybrid(s); and the second aliquot is annealed to a second set of different-sequence primers to produce a second set of target-primer hybrid(s), wherein at least one primer in the first set and at least one primer in the second set contain the same target binding segment and a different tag segment. The primers in each aliquot are then extended in the presence of a different nucleotide terminator, and the appended base type for a particular primer binding segment may be identified from the attached tag segment, without requiring different base labels.

In a further embodiment, the primer extension step is performed on a single sample in the simultaneous presence of at least two different nucleotide terminators that contain detectably different labels. Preferably, one or more nucleotide terminators contain a fluorescent or chemiluminescent label, preferably a fluorescent label.

In a preferred embodiment, at least one nucleotide terminator is a 2',3'-dideoxy-nucleotide.

In a particularly preferred embodiment, primer extension is performed in the presence of four different nucleotide terminators (corresponding to A, C, G, and T/U), each of which is labeled with a different label that identifies the base contained in the terminator. Preferably, the labels are fluorescent labels with four different emission wavelengths.

The sample may be any nucleic acid sample that is suitable for testing in accordance with the present invention. In particular, polynucleotides in the sample may be amplified by at least one cycle of polymerase chain reaction prior to contact with the tagged primers.

In another aspect, the invention also includes kits and reagents that may be used in any of the above methods. In one embodiment, the invention includes a kit that is useful for obtaining sequence information from a plurality of target polynucleotides in a sample, comprising (a) a set of different sequence primers, each of which contains (i) a target binding segment and (ii) a tag segment having a nucleotide sequence that identifies the target binding segment, (b) at least one labeled nucleotide terminator, and (c) a primer-extending reagent, under conditions effective to append the terminator to an end of the annealed primer in the hybrid only when the terminator is complementary to a base in the target polynucleotide that is immediately adjacent to the end of the annealed primer, to form an extended hybrid mixture. The kit may also include instructions for utilizing the kit in accordance with the invention, and/or an addressable array of immobilized, different tag complements, wherein each different tag complement contains a sequence that is complementary to the primer tag segments. Preferably, at least one labeled nucleotide terminator is a 2',3'-dideoxymononucleotide. In another embodiment, the kit includes a set of at least four differently labeled nucleotide terminators which are complementary to adenine, guanine, cytosine, and either thymine or uracil bases.

These and other objects and features of the invention will become more apparent when read in light of the accompanying drawings and the detailed description below.

DETAILED DESCRIPTION OF THE INVENTION

L. Definitions

The following terms and/or phrases as used herein are intended to have the meanings below unless indicated otherwise.

"Nucleoside" refers to a compound containing a base-pairing moiety (also referred to as a "base") such as a purine, deazapurine, or pyrimidine nucleoside base, e.g., adenine, guanine, cytosine, uracil, thymine, deazaadenine, deazaguanosine, or any functional equivalent thereof, which is attached to a backbone moiety such as a sugar, ring or any functional equivalent thereof. Nucleosides include naturally occurring nucleosides which contain a base-pairing moiety (A, C, G, T or U) linked to the 1'-carbon of a pentose ring, including 2'-deoxy and 2'-hydroxyl forms thereof (Kornberg, 1992), and to pentose analogs and ring-open equivalents thereof (Scheit, 1980; Uhlman, 1990).

The term "nucleotide" as used herein refers to a phosphate ester of a nucleoside, e.g., a triphosphate ester, wherein the most common site of esterification is the pentose 5'-hydroxyl group. In certain cases, term "nucleoside" refers both nucleosides and nucleotides, for convenience. The terms nucleotide and nucleoside as used herein are intended to include synthetic analogs having modified nucleoside base moieties, modified sugar moieties, and/or modified phosphate ester moieties, e.g., as described elsewhere (Scheit 1980; Eckstein, 1991).

"Polynucleotide" or "oligonucleotide" refer to a polymer of nucleoside monomers, including single, double and triple stranded deoxyribonucleotides, ribonucleotides, α-anomeric forms thereof, and the like. Usually the nucleoside monomers are linked by phosphodiester linkages, such that "phosphodiester linkage" refers to a phosphate ester bond or analog thereof wherein the phosphorous atom is in the +5 oxidation state and one or more of the oxygen atoms is replaced with a non-oxygen moiety. Exemplary phosphate analogs include phosphorothioate, phosphorodithioate, phosphoroselenoate, phosphorodiselenoate, phosphoroanilothioate, phosphoranilidate, phosphoramidate, boronophosphates, and the like, including associated counterions, e.g., $H^+$, $NH_4^+$, $Na^+$, and the like, if such counterions are present. "Polynucleotides" and "oligonucleotide" also include polymers of non-nucleotide monomers, linked by phosphate ester or other linkages, which are capable of forming sequence-specific hybrids with a target nucleic acid, e.g., peptide nucleic acids (PNAs; e.g., see Knudsen, 1996). Polynucleotides typically range in size from a few monomeric units, e.g. 8–40, to hundreds or thousands of monomeric units. Whenever a polynucleotide is represented by a sequence of letters, such as "ATGCCTG," it will be understood that the nucleotides are in 5' to 3' order from left to right and that "A" denotes deoxyadenosine, "C" denotes deoxycytidine, "G" denotes deoxyguanosine, and "T" denotes thymidine, unless otherwise noted.

"Primer" means a polynucleotide capable of selectively annealing to a specified target sequence and thereafter serving as a point of initiation of a primer extension reaction in the 5'→3' or 3'→5' direction.

"Primer extension reaction" means a reaction, between a target-primer hybrid and a nucleotide which results in the addition of the nucleotide to a selected-end of the primer such that the added nucleotide is complementary to the corresponding nucleotide in the target nucleic acid.

"Extendible primer" refers to a primer that is capable of having a nucleotide appended (covalently linked) to an extendable end of the primer.

"Target-specific primer" refers to a primer having a target-binding segment that is perfectly or substantially complementary to a target sequence, such that the primer binds specifically to an intended target without significant binding to non-target sequences under sufficiently stringent hybridization conditions.

"Nucleotide terminator" refers to a nucleotide or nucleoside that (1) is covalently linkable to an end of an extendible primer when the primer is annealed to a complementary template, but (2) is not capable of further extension under the conditions used to covalently link the nucleotide terminator to the primer.

"Specific binding pair" refers to a pair of molecules that specifically bind to one another to form a binding complex. Examples of specific binding pairs include, but are not limited to antibody-antigen (or hapten) pairs, ligand-receptor pairs, enzyme-substrate pairs, biotin-avidin pairs, polynucleotides having complementary base pairs, and the like.

"Primer extending reagent" means an enzyme or other catalyst capable of catalyzing a reaction leading to covalent attachment of a nucleotide terminator to an end of a primer when the primer is annealed to a complementary target nucleic acid.

"Label" means any moiety that, when attached to a nucleotide or polynucleotide of the invention, render such nucleotide or polynucleotide detectable using known detection means.

"Diagnosis" is intended to encompass diagnostic, prognostic, and screening methods.

II. Components

A. Sample Nucleic Acids

The target nucleic acids for use with the invention may be derived from any living or once living organisms, including but not limited to prokaryotes, eukaryotes, plants, animals, and viruses, as well as synthetic nucleic acids. The target nucleic acids may originate from any of a wide variety of sample types, such as cell nuclei (e.g., genomic DNA) and extranuclear nucleic acids, e.g., plasmids, mitrochondrial nucleic acids, and the like. The target nucleic acids can include DNA or RNA, and are usually DNA.

Many methods are available for the isolation and purification of target nucleic acids for use in the present invention. Preferably, the target nucleic acids are sufficiently free of proteins and any other interfering substances to allow target-specific primer annealing and extension. Preferred purification methods include (i) organic extraction followed by ethanol precipitation, e.g., using a phenol/chloroform organic reagent (Ausubel), preferably using an automated DNA extractor, e.g., a Model 341 DNA Extractor available from PE Applied Biosystems (Foster City, Calif.); (ii) solid phase adsorption methods (Walsh, 19911; Boom); and (iii) salt-induced DNA precipitation methods (Miller), such methods being typically referred to as "salting-out" methods. Optimally, each of the above purification methods is preceded by an enzyme digestion step to help eliminate protein from the sample, e.g., digestion with proteinase K, or other like proteases.

To facilitate detection, the target nucleic acid can be amplified using a suitable amplification procedure. Such amplification may be linear or exponential. In a preferred embodiment, amplification of the target nucleic acid is accomplished using the polymerase chain reaction (PCR) (Mullis). Generally, the PCR consists of an initial denaturation step which separates the strands of a double stranded nucleic acid sample, followed by repetition of (i) an annealing step, which allows amplification primers to anneal specifically to positions flanking a target sequence; (ii) an extension step which extends the primers in a 5'→3' direction thereby forming an amplicon nucleic acid complementary to the target sequence, and (iii) a denaturation step which causes the separation of the amplicon from the target sequence. Each of the above steps may be conducted at a different temperature, preferably using an automated thermocycler (PE Applied Biosystems, Foster City, Calif.).

B. Sequencing Reagents

In one aspect, the invention utilizes a plurality of extendable, different-sequence primers for detecting target sequences of interests. In one embodiment, the tagged primer includes a target binding segment, a tag segment, and an extendable primer end (5' or 3'). The target binding segment includes a polynucleotide sequence which is selected to bind to a selected target sequence. The tag segment contains a unique polynucleotide sequence that allows identification of the target binding segment to which the tag segment is attached. The tag segment can be directly attached to the distal end of the target binding segment, or is optionally linked to the tag segment by an intervening spacer group. In another embodiment, the tag segment is linked to an internal site within the target binding segment. Thus, the tag can be linked to an intersubunit linking group, or to a nucleotide base, within the target binding segment. Preferably, the tag is attached to an end of the target binding segment that is distal with respect to the extendable end of the primer.

The primers can be prepared by any suitable method, preferably using an automated DNA synthesizer, e.g., PE Applied Biosystems (Foster City, Calif.) model 392 or 394 DNA/RNA Synthesizer, using standard chemistries, e.g., phosphoramidite chemistry (Beaucage; Gait, 1984, 1990). In an alternative method, primers can be isolated from biological sources.

The sequence of each target binding segment is selected to hybridize to a selected complementary target which contains a potential polymorphism or mutation, such that the potential polymorphism or mutation is located immediately adjacent to (immediately flanking) the terminal base at the extendable end of the primer. The length of the target binding segment in each primer is selected to ensure specific hybridization of the primer to the desired target, without significant cross-hybridization to non-target nucleic acids in the sample. Also, to enhance primer specificity, it is preferred that the melting temperatures of the target binding segments are within a few degrees of each other. Preferably, the melting temperatures of the target binding segments fall within a ΔTm range (Tmax−Tmin) of 10° C. or less, and preferably 50° C. or less. This can be accomplished by suitable choice of binding segment lengths based on known methods for predicting primer melting temperatures (Breslauer, 1986; Rychlik, 1989 and 1990; Wetmur, 1991; Osborne, 1991; Montpetit, 1992) for example. Target binding segments between about 18 and 24 bases in length are preferred because such polynucleotides tend to be very sequence-specific when the annealing temperature is set within a few degrees, of a primer melting temperature (Dieffenbach, 1995).

The tag segment in each tagged primer is designed to contain a sequence that uniquely identifies the attached target binding segment. Thus, the tag sequences should be selected to minimize (1) internal, self-hybridization, (2) hybridization with other same-sequence tags, (3) hybridization with other, different sequence tag complements, (4) and hybridization with the sample polynucleotides. Also, it is preferred that each tag can specifically recognize and hybridize to its corresponding tag complement under the same conditions for all tags in the primers.

Tag sequences can be selected by any suitable method. For example, computer algorithms for selected non-crosshybridizing sets of tags are described in Brenner (1996) and Shoemaker (1997). Preferably, the tag sequences have strands that are within a preselected temperature range, as discussed above with respect to the extendable primers. Preferably, the melting temperatures of the target binding segments fall within a ΔTm range (Tmax−Tmin) of 10° C. or less, and preferably within 50° C. or less, as calculated using any of the methods above (e.g., Breslauer). Preferably, the tag segments are at least 12 bases in length to facilitate specific hybridization to corresponding tag complements. Typically, tag segments are from 12 to 60 bases in length, and typically from 15 to 30 bases in length.

As discussed above, each target binding segment is extendable, meaning that a nucleotide terminator can be appended to one of the ends of the target binding segment when the target binding segment is hybridized to a complementary target sequence, if the nucleotide terminator is complementary to a corresponding base in the target sequence that is immediately adjacent to the extendable end of the hybridized tag primer. Typically, the extendable end of the primer is located at the 3'-terminus of the target binding segment, such that the 3'-terminal base contains a 3'-hydroxyl, 3'-amino, or other reactive group that can be covalently linked to a nucleotide terminator by a primer extending reagent. Alternatively, the primers contain 5'-extendable ends.

The target base to be detected is any base that is sufficient to identify the presence of a if polymorphism or mutation in a target polynucleotide, to identify a particular allele, or to exclude the presence of a potential target sequence. For example, in a genomic DNA target, the target base can be a single nucleotide polymorphism (SNP) that is associated with the occurrence of a particular disease, with an HLA type, or with any other genotypic or phenotypic trait. As further illustration, the target base can define (1) the terminus of a sequence insert; (2) the terminus of a remote region that has been spliced to the primer-complementary region in the target as the result of a deletion of one or more target bases; or (3) the terminus of a mis-spliced mRNA segment, for example.

The labeled nucleotide terminator that is used to identify or detect the target base of interest is any nucleoside that is complementary to the target base and is capable of being covalently linked to the extendable end of the target-specific primer when the primer is specifically annealed to a target polynucleotide. For covalent linkage to a primer having an extendable 3'-end, the nucleotide terminator (1) contains a suitable 5'-reactive group, such as a 5'-triphosphate moiety for reaction with a primer 3'-hydroxyl group, and (2) is incapable of further extension in the 3'-direction, e.g., by having a 3'-deoxy substituent or 3'-hydroxy-blocking group in a ribose or deoxyribose ring instead of a 3'-hydroxyl group. Examples of 3'-deoxy substituents include hydrogen, 3'-fluoro, 3'-amino, and 3'-azido, for example (Mikhailopulo et al., 1989; Krayevski et al., 1984; Chidgeavadze, 1986). Examples of 3'-hydroxy blocking groups include phosphate, phosphonate, t-Boc, and O-acetyl, for example. For covalent linkage to a primer having an extendable 5'-end, the nucleotide terminator (1) contains a suitable 3'-reactive group, such as a 3'-hydroxyl for reaction with a primer 5'-triphosphate group, and (2) is incapable of further extension in the 5'-direction, e.g., due to the absence of a 5'-triphosphate or other extendable 5'-moiety.

One requirement of a nucleotide terminator is that when the nucleotide terminator contains a ribose moiety, the 3'-carbon must not have a free hydroxy group capable of being used subsequently by a polymerase to attach additional nucleotides. Alternatively, a ribofuranose analog can be used, such as arabinose. Exemplary nucleotide terminators include 2',3'-dideoxy-β-D-ribofuranosyl, β-D-arabinofuranosyl, 3'-deoxy-β-D-arabinofuranosyl, 3'-amino-2',3'-dideoxy-β-D-ribofuranosyl, and 2',3'-dideoxy-3'-fluoro-β-D-ribofuranosyl (e.g., Chidgeavadze, 1984, 1985). Nucleotide terminators can also include reversible nucleotide terminators (Metzker, 1994).

Each nucleotide terminator includes a detectable label moiety which allows determination of whether the nucleotide terminator has been appended to a target-specific primer. Labels may be direct labels which themselves are detectable or indirect labels which are detectable in combination with other agents. Exemplary direct labels include but are not limited to fluorophores, chromophores, radioisotopes (e.g., $^{32}P$, $^{35}S$, $^{3}H$), spin-labels, chemiluminescent labels, and the like. Exemplary indirect labels include enzymes which catalyze a signal-producing event, and ligands such as an antigen or biotin which can bind specifically with high affinity to a detectable anti-ligand, such as a labeled antibody or avidin. Many comprehensive reviews of methodologies for labeling DNA provide guidance applicable to the present invention. Such reviews include Matthews et al. (1988); Haugland (1992), Keller and Manak (1993); Eckstein (1991); and the like. Additional methods for creating labeled nucleotide terminators, particularly fluorescent labels, are described in Fung et al., Hobbs et al., Menchen et al., and Bergot et al., and Rosenblum et al. (all supra).

In one embodiment, the primer extending reagent is a DNA polymerase enzyme. Exemplary polymerase enzymes include, but are not limited to, Pfu DNA polymerase, *E. coli* polymerase I, T-7 polymerase, reverse transcriptase, Taq DNA polymerase, TAQ FS polymerase, and the like (Kornberg and Baker). RNA polymerases and reverse-transcriptases can also be used, e.g., for RNA primers.

The invention also utilizes a set of tag complements which are complementary to corresponding tag sequences in the tagged primers. The tag complements are provided as an addressable array, according to the design choice of the user. By "addressable array" is meant that the sequence of the target binding segment of each primer is known or can be determined from the position of hybridization of each primer on the array. Preferably, the tag complements are immobilized in discrete regions on a planar surface, such that each discrete region contains only tag complements having a particular sequence, and such that the sequence of the tag complement at each different discrete region is known. Conveniently, the tag complements are distributed as a periodic two-dimensional array of discrete tag complement regions which can be indexed via X and Y coordinates, or any equivalent thereof.

The solid phase support can be formed using any material that allows for the tag segments to hybridize specifically to their complementary tag complements on the support glass; quartz; silicon; polycarbonate; a metallic material, such as GaAs, copper, or germanium; a polymerized gel, such as crosslinked polyacrylamide; or a membrane, such as nylon, polyvinylidine difluoride (PVDF), or polytetrafluoroethylene.

Immobilization of the tag-complements within the array is accomplished using any of a variety of suitable methods. In one approach, the tag complements are deposited onto a solid phase surface using known liquid dispensing methods. For example, deposition can be accomplished robotically on a poly-lysine-coated microscope slide, followed by treatment with succinic anhydride to couple the tag complements to the polylysine moieties, as described by Schena et al. (1995) and Shalon (1995). For covalent attachment, the tag-complements may include a suitably reactive functionality for covalent attachment to the support. Exemplary linking chemistries are disclosed in Barany et al. (1991), Pon et al. (1988), and Menchen et al. (1994).

In another approach, tag complements can be synthesized on a support by photolithographic methods, as described in Fodor et al. (1991, 1995), Pirrung et al. (supra), and Shoemaker (1997). Photoremovable groups are attached to a substrate surface, and light-impermeable masks are used to control the addition of monomers to selected regions of the substrate surface by activating light-exposed regions. Monomer addition to the growing polymer chains is continued using different mask arrangements until the desired, different sequence tag complements are formed at the desired addressable locations. The masking method of Fodor et al. may also be modified to accommodate block-polymer synthesis. For example, an array of linker groups (e.g., a polypeptide, or an N-protected aminocaproic acid linked to an aminopropyl group) can be formed on the substrate surface via simultaneous activation of all immobilization regions to form a "carpet" of linker groups. The tag complements are then individually deposited on (or adsorbed to) the substrate surface as liquid drops at selected addressable locations, and are exposed to light or heat as appropriate to couple the binding moieties to the immobilized linker groups, preferably while a sufficient amount of solvent still remains from each drop.

Alternatively, the tag complements may be immobilized on the support(s) non-covalently, e.g., using ligand-receptor type interactions. For example, the tag complements may contain covalently attached biotin groups as linker groups, for binding to avidin or streptavidin polypeptides which have been attached to a support (e.g., Barrett, 1996).

Linker segments may also be included between the tag complement sequence and the support to provide a spacer arm which allows the tag-specific binding region to separate from the support, rendering the binding region more accessible to the sample. Exemplary linker groups are described, for example, in Fodor et al. (1995), Brenner (supra), and the Examples herein (polyethylene oxide polymers). Preferably, the tag complement segment is separated from the support by a chain comprising at least 10 chain atoms.

The support may include depressions in the support for holding the deposited tag complements. Elevated protrusions can also be used, onto which the tag complements are deposited. In yet another approach, the tag complements are attached to an array of individual beads attached to a surface, via magnetic force if the beads are magnetic (Albretsen, 1990), or with an adhesive, for example.

In another approach, an array is formed on a substrate, such as a glass plate, which is covered with a rectangular array of pieces of polyacrylamide gel (e.g., Khrapko et al., 1991). A different tag complements is deposited at a selected site and is bound thereto by reacting a 3'-terminal dialdehyde on the tag complements with hydrazide groups on the polyacrylamide gel piece. Tag complement arrays in accordance with the invention may also be formed by robotic deposition of tag complements onto nylon (Khrapko et al., supra). Following deposition, immobilization of the tag complements may be facilitated by heat or photoactivation as appropriate.

To reduce the amounts of assay reagents used for tag detection, and to facilitate the sequencing of large numbers of fragment sequences, the arrays are preferably formed as microarrays having tag complement region densities of greater than 100 regions/$cm^2$, 300 regions/$cm^2$, $10^3$ regions/$cm^2$, $3 \times 10^3$ regions/$cm^2$, $10^4$ regions/$cm^2$, $10^5$ regions/$cm^2$, or $10^6$ regions/$cm^2$. In addition, the number of different sequence tag complements in each array is preferably equal to or greater than 10, 20, 50, 100, 200, 500, 1000, 3000, 10,000, 30,000, 100,000, or 300,000.

The tags and tag complements may be single or double stranded, such that sequence specific hybridization forms either duplexes by Watson and Crick base-pairing, or triplexes by forward or reverse Hoogsteen bonding. In embodiments where specific hybridization occurs via triplex formation, coding of tag sequences follows the same principles as for duplex-forming tags; however, there are further constraints on the selection of word sequences. Generally, third strand association via Hoogsteen type of binding is most stable along homopyrimidine-homopurine tracks in a double stranded target. Usually, base triplets form in T-A*T or C-G*C motifs (where "-" indicates Watson-Crick pairing and "*" indicates Hoogsteen type of binding); however, other motifs are also possible. For example, Hoogsteen base pairing permits parallel and antiparallel orientations between the third strand (the Hoogsteen strand) and the purine-rich strand of the duplex to which the third strand binds, depending on conditions and the composition of the strands.

There is extensive guidance in the literature for selecting appropriate sequences, orientation, conditions, nucleoside type (e.g. whether ribose or deoxyribose nucleosides are employed), base modifications (e.g. methylated cytosine, and the like in order to maximize, or otherwise regulate, triplex stability as desired in particular embodiments, e.g., Brenner (supra). More generally, conditions for annealing single-stranded or duplex tags to single-stranded or duplex sequence complements are well known, e.g. Brenner (supra), Ji et al. (1993), Cantor et al. (supra), Wetmur (1991), Breslauer et al. (1986), Schena (1995), and the like.

II. Detection and Identification Methods

In one aspect, the invention includes a method for obtaining sequence information from a plurality of target polynucleotides in a sample.

In one embodiment, the method involves contacting a plurality of different sequence primers with a polynucleotide sample under conditions effective for the primers to anneal to primer-complementary regions in one or more target polynucleotides, to form one or more target-primer hybrid (s). Each different-sequence primer contains (i) a target binding segment and (ii) a tag segment having a nucleotide sequence that identifies the target binding segment.

As discussed in the preceding section, conditions for hybridizing primers to polynucleotide targets are well known. The annealing reaction is performed under conditions which are stringent enough to guarantee sequence specificity yet sufficiently permissive to allow formation of stable hybrids at an acceptable rate. The temperature and length of time required for primer annealing depend upon several factors including the base composition, length and concentration of the primer, and the nature of the solvent used, e.g., the concentration of cosolvents such as DMSO (dimethylsulfoxide), formamide, or glycerol, and counterions such as magnesium. Typically, hybridization (annealing) with synthetic polynucleotides is carried out at a temperature that is approximately 5 to 10° C. below the melting temperature of the target-primer hybrid in the annealing solvent. Typically, the annealing temperature is in the range of 55 to 75° C. and the primer concentration is approximately 0.2 $\mu$M. Under such conditions, the annealing reaction is usually complete within a few seconds (e.g., Example 1).

The resultant hybrid(s) are contacted with a labeled nucleotide terminator in the presence of a primer-extending reagent, under conditions effective to append the terminator to an end of the annealed primer in the hybrid only when the terminator is complementary to a base in the target polynucleotide that is immediately adjacent to the end of the annealed primer, to form an extended hybrid mixture. Preferably, for use with a 3'-extendable primer, the primer-extending reagent is a DNA or RNA polymerase, and the labeled nucleotide terminator contains a 5'-triphosphate group to facilitate covalent linkage to a 3'-hydroxyl group of the primer. Conditions for adding nucleotides to annealed primers using nucleic acid polymerases are well known (e.g., Ausubel, Sambrook).

In some cases, the target polymorphism is one of two or more possible alternative bases. Thus, reacting an annealed primer with the corresponding two or more different complementary terminators in the presence of an extension reagent will be sufficient to identify at least one of the possible alternative sequences. Similarly, if the target polymorphism is one of three or four possible alternatives, the annealed primer should be reacted with the appropriate number of possible base alternatives to confirm which possible sequences are actually present. In Examples 1 and 2 below, four different target-specific primers were each extended in the presence of four different nucleotide terminators labeled with distinguishing fluorescent labels, and in each case, only the correct terminators were appended to each primer.

In one embodiment, primer extension is accomplished by dividing the hybridization mixture into two or more aliquots, and each aliquot is reacted with a different, single nucleotide terminator base-type. For example, the hybridization mixture can be divided into four aliquots, and each aliquot is reacted with a selected terminator equivalent to A, C, G or T/U. Using this approach, all terminators can contain the same label, provided that (i) the extension reactions for each different terminator type are kept separate from each other, or (ii) the primer for each target contains a tag segment that identifies both the primer sequence and the terminator type. Preferably, the hybridization, mixture is reacted simultaneously with a set of four terminator types encompassing A, C, G and T, and which have distinct labels to identify each terminator type.

In another embodiment, prior to immobilization on a tag complement array, multiple cycles of primer extension can be carried out to amplify the amounts of extended primer products for easier detection. Thus, after the first extension reaction, the primers (extended and non-extended) can be denatured from the target polynucleotides by appropriate means (e.g., by heating the extension reaction well above the melting temperatures of the extended primers), followed by annealing of new, non-extended primers onto the target polynucleotides and primer extension. Since the non-extended primers are usually present in excess relative to the target polynucleotides, the amount of extended primers that reanneal to the target polynucleotides is usually insignificant. In Examples 1 and 2, extension mixtures were cycled 50 times with the following cycle: 95° C. for 10 sec (denaturation), 45° C. for 5 sec (primer annealing), and 60° C. for 1 minute (extension).

The extended (and non-extended) primers can then be immobilized on an addressable array of immobilized, different tag complements, under conditions effective to hybridize the primers to corresponding tag complements, as discussed above. Each different tag complement contains a sequence that is complementary to one of the primer tag segments. The different primers hybridize to tag complements located at discrete regions in the array, such that the identity of each immobilized target-specific primer can be determined from its location in the array.

The identification of a nucleotide terminator appended to at least one extended primer immobilized on the array allows determination of the presence of at least one target sequence in the sample. Appended nucleotide terminators can be identified by any suitable method, for example: (i) on the basis of different terminator-specific labels attached to the terminators (e.g., fluorescent dyes having different emission wavelengths), (ii) by using different tags to identify the terminator base-type that might be appended to a particular primer, (iii) using a combination of different terminators and tags, or (iv) if the same label is used for all terminators, by performing extensions in the presence of each different terminator separately and analyzing the products of each extension reaction separately.

Any detection method may be used which is suitable for the type of label employed. Thus, exemplary detection methods include radioactive detection, optical absorbance detection, e.g., UV-Visible absorbance detection, optical emission detection, e.g., fluorescence or chemiluminescence. For example, extended primers can be detected on an array by scanning all or portions of each array simultaneously or serially, depending on the scanning method used. For fluorescence labeling, selected regions on an array may be serially scanned one-by-one or row-by-row using a fluorescence microscope apparatus, such as described in Fodor (1995) and Mathies et al. (1992). Hybridization patterns may also be scanned using a CCD camera (e.g., Model TE/CCD512SF, Princeton Instruments, Trenton, N.J.) with suitable optics (Ploem, 1993), such as described in Yershov et al. (1996), or may be imaged by TV monitoring (Khrapko, 1991). For radioactive signals (e.g., $^{32}$P), a phsphorimager device can be used (Johnston et al., 1990; Drmanac et al., 1992; 1993). Other commercial suppliers of imaging instruments include General Scanning Inc., (Watertown, Mass. www.genscan.com), Genix Technologies (Waterloo, Ontario, Canada; www.confocal.com), and Applied Precision Inc. Such detection methods are particularly useful to achieve simultaneous scanning of multiple tag complement regions.

Measured signals can be analyzed manually or by appropriate computer methods to tabulate results. For heterozygous target sequences which produce two or more extension products due to the presence of different alleles, superimposed fluorescent signals from the same array region may be observed that can be deconvoluted based upon the distinctive fluorescence emission characteristics of different terminator dyes. The results can be measured to provide qualitative or quantitative results, depending, on the needs of the user. The arrays and reaction conditions can include appropriate controls for verifying the integrity of hybridization and extension conditions, and for providing standard curves for quantitation, if desired. For example, a control primer can be added to the polynucleotide sample for extending a target polynucleotide sequence that is known to be present in the sample (or a target polynucleotide sequence that is added to the sample). The absence of the expected extension product is an indication that there is a defect with the sample or assay components requiring correction.

III. Sequencing Kits

In another aspect, the invention also includes kits and reagents that may be used in any of the above methods. In one embodiment, the invention includes a kit that is useful for obtaining sequence information from a plurality of target polynucleotides in a sample, comprising (a) a set of different-sequence primers, each of which contains (i) a target binding segment and (ii) a tag segment having a nucleotide sequence that identifies the target binding segment, (b) at least one labeled nucleotide terminator, and (c) a primer-extending reagent, under conditions effective to append the terminator to an end of the annealed primer in the hybrid only when the terminator is complementary to a base in the target polynucleotide that is immediately adjacent to the end of the annealed primer, to form an extended hybrid mixture. The kit may also include instructions for utilizing the kit in accordance with the invention, and/or an addressable array of immobilized, different tag complements, wherein each different tag complement contains a sequence that is complementary to the primer tag segments. Preferably, at least one labeled nucleotide terminator is a 2',3'-dideoxymononucleotide. In another embodiment, the kit includes a set of at least four differently labeled nucleotide terminators which are complementary to adenine, guanine, cytosine, and either thymine or uracil bases, and which are preferably 2',3'-dideoxy terminators. Preferably, the primer-extending reagent is a DNA polymerase. The kit may additionally include a buffer solution for facilitating primer extension, and/or at least one extendable control primer for annealing to a control target polynucleotide sequence and extension with an appropriate labeled nucleotide terminator, to verify whether the reaction conditions are appropriate to extend primers that are annealed to their respective targets.

From the foregoing, it can be appreciated how various objects and features of the invention are met. The invention provides a convenient method for determining the presence or absence of a plurality of target polymorphic sequences in a sample. The method is amenable to high-throughput processing of many target primers and many different samples. By using a universal array of tag complements, only a single set of hybridization conditions is necessary, and the need to make customized arrays for particular target sequences is avoided. Furthermore, by performing primer extension reactions in solution phase, greater consistency in results can be obtained. The invention is highly advantageous for providing extensive sequence information about a sample, which can be used for a variety of purposes, such as genetic screening, gene typing, sample identification, disease diagnosis, forensics, and many others.

The invention may be further understood in light of the following examples, which are not intended to limit the invention.

EXAMPLE 1

Preparation of Addressable Array

A. Addressable Array

Glass microscope slides were immersed in 1 N HNO$_3$ for 1 to 2 hours, followed by rinsing with deionized water. Optionally, slides were soaked overnight in 5% HCl to improve long-term stability of subsequent functionalization. Slides were then sonicated sequentially in the following three solvents for 10 minutes each: hexane, acetone, and ethanol, followed by drying in air.

A solution of 2% (v/v) aminopropyltriethoxy silane (0.8 mL in 40 mL) in 95% acetone:5% water was prepared in a disposable plastic Falcon tube. This amount of solution was usually sufficient to coat at least three slides. The solution was allowed to stand for 5 to 20 minutes to hydrolyze the ethoxy groups to hydroxyl groups. Air-dried slides were dipped in the solution for 2 minutes each, and then rinsed by dipping in three or more successive acetone baths.

The slides were cured in 100° C. oven for 45 minutes. Cured slides were treated for 2 hours with a 0.2% solution of 1,4-phenylene diisothiocyanate (PDITC) in 10% pyridine:dimethyl formamide, followed by washes in baths of methanol and acetone, and air-drying. The slides may be stored under vacuum with a desiccant at 4° C. Stacking the slides also helps preserve the functionalization and keeps the functinalized surfaces free from particulates. (In an alternative embodiment, instead of 1,4-phenylene diisothiocyanate, the cured slides can be treated with a 1 mM solution of EMCS (N-(,-maleimido caproxyl) succinimide in methanol:dimethylsulfoxide (80:20) for 2 hours.)

Tag complements were prepared by standard phosphoramidite synthetic methods. The tag complements had the following general structure: 5'-amino-[(PEO)$_2$]-[tag complement (24 nt)], where PEO=-O-(CH$_2$CH$_2$O)$_6$ added via DMT-O-(CH$_2$CH$_2$O)$_6$-phosphoramidite, such that the sequences of the tag complements were perfectly complementary to the tag segments in primers 1 through 4 noted in Example 1B, such that tag segments would bind with their 5'-ends closest to, the solid support. The tag complements were spotted in a rectangular array pattern onto slides prepared as above using an ASYMTEC robotic loader. (Asymtec, Carlsbad, Calif., Model No. C-708), with oligonucleotide (tag complement) concentrations of about 50 $\mu$M (in 100 mM Na$_2$CO$_3$, pH 9.0) and spotting volumes of about 0.2 to 1 nL. The pattern included a separate set of 4 spots for each different tag complement to provide redundancy. The spots had diameters of about 200 micrometers each and were spaced apart by 320 micrometers center-to-center. The robotic loader included a slide holder to hold the slides during oligonucleotide deposition, and a blotting area for cleaning dispenser tips.

After spotting, the tag complements were fixed onto the slides by incubating the slides in a humidity chamber at room temperature for 60 minutes, followed by soaking in 1% NH$_4$OH (aq) for 20 minutes and in 0.2% casein in TBS (50 mM Tris, 150 mM NaCl, pH 8) for 20 minutes. The slides were washed in deionized water and stored at 4° C.

B. Primer Extension

Expression vector pGEM32f(+)was obtained from Promega (Madison, Wis.). Four primers were synthesized that were specific for four different regions of the pGEM plasmid, so that extension of each primer would incorporate a different 2'-3'-dideoxynucleotide (ddNTP). The primers contained target binding segments 18–23 nucleotides in length, with a different tag segment (24 nucleotides) attached directly to the 5'-end of each target-binding segment. The sequences of the tagged primers were as follows:

1) primer Z996SP6(A) (extension base is A), SEQ ID NO:1:
   5'-TGATGATTGATTGTATGATTTTGAATTTAGGTG ACACTATAG-3'
2) primer Z1045T7(T) (extension base is T), SEQ ID NO:2:
   5' -TGATGATTAAAGAAAGTTGAGTATAATACGA CTCACTATAGGGCGAA-3'
3) primer Z1082m13(G) (extension base is G), SEQ ID NO:3:
   5'-TGATGATTTGTAGTATGTATAAAGTGTAAAAC GACGGCCAGT-3'
4) primer Z1128MS(C) (extension base is C), SEQ ID NO:4:
   5'-TGATGATTTTGATGTAAAAGTTGAAGCTCGG TACCCGGGGATC-3' where single underlining indicates tag segments, and non-underlined segments are primer-binding segments.

Extension reactions were performed separately for each tagged primer using the following components:

| | |
|---|---|
| Template (pGEM) | 3 $\mu$L (60 ng) |
| Primer | 2 $\mu$L (2 pm) |
| Dideoxy mix | 2 $\mu$L |
| 5x Seq. Buffer | 2 $\mu$L |
| Water | 11 $\mu$L |
| TAQ FS | 0.5 $\mu$L (4 Units) |
| Total Volume: | 20.5 $\mu$L |

The dideoxy mix contained 1.075 $\mu$M ddATP(R6G), 1.5 $\mu$M ddCTP(Rox), 1.05 $\mu$M ddGTP(Tamra), and 11.25 $\mu$M ddTTP(R110), where the indications in parentheses identify the attached "BIG DYE" fluorescent label (Perkin-Elmer Corp., Foster City, Calif.; Rosenblum et al., 1997). The 5x sequencing buffer contained 400 mM Tris, pH 9.0, and 10 mM MgCl$_2$. Each extension reaction mixture was cycled 50 times on a Perkin Elmer GENEAMP 9600 System with the following cycle: 95° C. for 10 sec, 45° C. for 5 sec, 60° C. for 1 minute. After the last cycle, each reaction mixture was passed through a "CENTRI-SEP" column (Princeton Separations, N.J.) to remove unincorporated dideoxynucleotides. The collected extension products from the four reactions were combined and dried in a miicrocentrifuge (Savant). The dried sample was resuspended in 27 $\mu$L water, and 3 $\mu$L PCR Buffer II was added (Perkin Elmer). This solution was applied to the addressable glass slide array from Example 1A, and the extended primers were hybridized to the immobilized tag complements by heating the slide to 80° C. for 1 sec, and then incubating at 33° C. for 20 minutes. Unbound materials were washed from the array by soaking the slide in TE (10 mM Tris, pH 8, 1 mM EDTA) for 2–5 minutes at room temperature (about 22° C.).

The slides were each viewed using an imaging device set for fluorescence emission detection at 560 nm and 610 nm. Prior to signal detection, the slides were overlaid with a viewing buffer containing 50% (w:v) urea and 1× TBE (0.09 M Tris-borate, 2 mM EDTA, pH~8.3), to provide an alkaline pH environment to enhance the fluorescence emissions of the dye labels.

The imaging device was an imaging fluorimeter that produces a two-dimensional image array of emission intensities (electronic image). Each point in the image array corresponds to a physical location on the sample slide. The excitation source is a 40 mW argon ion laser. The excitation wavelength can be selected from either of two natural laser lines. (488 nm and/or 514 nm). The selection of laser wavelengths is accomplished by passing the beam which contains light of both wavelengths through one of three filters. The selected filter will pass either 488 nm only, 514 nm only, or both 488 and 514 nm. The filters are mounted on a motor-driven platform so that the selection can be performed under computer control. The beam containing either or both wavelengths passes through a classical beam expander. The collimated expanded beam is then directed into a commercially available assembly (Scanlab, Puchhein, Germany, Model SK1020) containing two orthogonal "galvo mirrors". This is a mechanical device designed to rotate each of the two mirrors quickly and precisely over a small angle. The axes of rotation are orthoganal and independent so that the beam can be rastered over a rectangular pattern, also under computer control.

The scanned beam is focused by an f-theta lens which forms a scanned laser spot at one focal length. The spot size is 20 $\mu$m diameter. Typically, it is stepped over an area of 20 mm×20 mm in increments of 20 $\mu$m, thereby forming a 1000×1000 array of pixels. The focused laser spot is formed after passing through a dichroic beam splitter which is designed to reflected the laser excitation wavelengths but transmit the fluorophore emission.

As the laser beam steps across a fluorescent region, the fraction of fluorescence radiation within the solid angle of collection of the emission optics is transmitted by the dichroic mirror and is collimated by a lens having a 150 mm focal length. The collimated beam is then filtered by a long pass interference filter which further rejects laser light. A second lens of 75 mm focal length focuses the beam onto the photocathode of a red sensitive photomultiplier tube (PMT). The PMT photocathode is not carefully adjusted since the focus is not critical. A filter wheel in front of the PMT allows only a small wavelength band (10 nm) to reach the detector. The filter wheel can be adjusted to one of six positions to allow for emission of multiple fluorophores to be discriminated.

The electrical output of the PMT is proportional to the intensity of the light reaching the photocathode. The computer system is capable of storing the signals at each of an array of mirror positions to form the electronic image.

The resultant images showed that for each tagged primer, only the expected terminator type was detectable at either 560 nm or 610 nm, to the exclusion of the other three terminators in the reaction mixture. For example, for the array regions containing appropriate tag complements for capturing Z996SP6(A) primer one, the detected fluorescent signal corresponded to the addition of a ddA terminator to the primer, to the exclusion of ddC, ddG and ddT.

EXAMPLE 2

Detection on Array Formed on Polymer Matrix

Glass microscope slides ("RITE-ON" from Becton Dickenson) were coated with a silanizing reagent by squirting the slides with 100 µL of gamma-methacryloxypropyltrimethoxy silane (Aldrich, 2% in $CHCl_3$), and then wiping the slide with a Kimwipe. Any dust was removed by a stream of air, after which the slides were allowed to air-dry.

An acrylamide/acrylic acid solution was prepared containing 5% (w:v) acrylamide/bis acrylamide (19:1 w:w mixture) and 1% acrylic acid in water. To 1 mL of this mixture was added 30 µL of 2% ammonium persulfate (APS) for radical generation. The solution was optionally filtered prior to addition of APS to remove any particles that were present. After addition of APS, TEMED was added to initiate polymerization in the mixture (1 µL TEMED per 100 µL APS/acrylamide solution). 20 µL of the polymerization mixture was applied to a surface of each slide, and a cover slip (pretreated with dichlorodimethyl silane to inhibit adhesion to the polymerizing gel) was placed carefully over the slide surface so that bubble formation was avoided. The covered slides were then placed on a 65° C. heating block for 5 minutes (a lower temperature, or a lower amount of TEMED, may be sufficient to promote polymerization for higher concentrations of acrylamide). After heating, the slides were removed from the heat block, the cover slips were removed, and the polymerized gels were allowed to air-dry. Optionally, the gel-coated slides were stored dry.

Coated slides were activated by soaking the slides for 1 hour in a 40 mL jar containing 0.1 M MES buffer (2-[N-morpholino]ethanesulfonic acid), pH 6.0, 50 mM EDC (1-ethyl-3-(3-dimethylaminopropyl carbodiimide), and 1 mM NHS (N-hydroxy succinimide) at room temperature. After soaking, the slides were rinsed with water and allowed to air-dry. The activated slides were spotted on the same day or were stored under cold, dry conditions for later use.

For sequence-detection, the slides were spotted with tag complements complementary to primers 1 through 4 in a rectangular array pattern as described in Example 1.

Extension reactions were performed separately for each tagged primer as described in Example 1B. After the reaction mixtures were recombined, the resultant mixture was applied to the tag array on the polymer-coated slide, and the extended primers were hybridized to the immobilized tag complements and visualized as described in Example 1B. The resultant images showed that for each tagged primer, only the expected terminator type was detectable at either 560 nm or 610 nm, to the exclusion of the other three terminators in the reaction mixture.

Although the invention has been described with respect to particular embodiments, it will be appreciated that various modifications can be made without departing from the spirit of the invention.

What is claimed is:

1. A method for obtaining sequence information from a plurality of target polynucleotides in a sample, the method comprising:

(a) contacting a plurality of different sequence primers with a polynucleotide sample under conditions effective for said primers to anneal to primer-complementary regions in one or more target polynucleotides, to form one or more target-primer hybrid(s), wherein each different-sequence primer contains (i) a target binding segment and (ii) a tag segment having a nucleotide sequence that uniquely identifies the target binding segment, (b) contacting said hybrid(s) with a labeled nucleotide terminator in the presence of a primer-extending reagent, under conditions effective to append said terminator to an end of the annealed primer in said hybrid only when said terminator is complementary to a base in the target polynucleotide that is immediately adjacent said end of the annealed primer, to form an extended hybrid mixture, (c) immobilizing said primers from the extended hybrid mixture on an addressable array of immobilized, different tag complements wherein each different tag complement contains a sequence that is complementary to said primer tag segments, under conditions effective to hybridize said primers to corresponding tag complements, and (d) identifying a nucleotide terminator appended to at least one extended primer immobilized on the array, thereby obtaining sequence information for at least one target sequence in the sample.

2. The method of claim 1, wherein step (b) includes contacting said hybrid(s) with at least two different nucleotide terminators which contain detectably different labels.

3. The method of claim 2, wherein said nucleotide terminators are contacted simultaneously, in the same reaction mixture, with said hybrid(s).

4. The method of claim 1, wherein step (a) further includes contacting a first set of different-sequence primers with a first sample aliquot to produce a first set of target-primer hybrid(s), and contacting a second set of different-sequence primers with a second sample aliquot to produce a second set of target-primer hybrid(s), wherein at least one primer in the first set and at least one primer in the second set contain the same target binding segment and a different tag segment.

5. The method of claim 4, herein step (b) further includes contacting the first set of hybrid(s) with a first nucleotide terminator, and reacting the second set of hybrid(s) with a second nucleotide terminator, wherein said first and second nucleotide terminators contain detectably different labels.

6. The method of claim 1, wherein said tag segments are at least 12 bases in length.

7. The method of claim 6, wherein said tag segments are from 12 to 60 bases in length.

8. The method of claim 1, wherein said nucleotide terminators are 2',3'-dideoxynucleotides.

9. The method of claim 1, wherein at least one nucleotide terminator contains a fluorescent label.

10. The method of claim 1, wherein at least one nucleotide terminator contains a chemiluminescent label.

11. The method of claim 1, wherein the polynucleotide sample is amplified by at least one cycle of polymerase chain reaction prior to step (a).

12. The method of claim 1, wherein instep (b), at least two cycles of primer annealing and extension are performed, to amplify the levels of extended primers.

* * * * *